United States Patent [19]

Raghunathan

[11] Patent Number: 4,847,077

[45] Date of Patent: Jul. 11, 1989

[54] CONTROLLED RELEASE PHARMACEUTICAL PREPARATIONS

[75] Inventor: Yegnaswami Raghunathan, Perinton, N.Y.

[73] Assignee: Pennwalt Corporation, Philadelphia, Pa.

[21] Appl. No.: 7,299

[22] Filed: Jan. 27, 1987

Related U.S. Application Data

[63] Continuation of Ser. No. 631,979, Jul. 18, 1984, abandoned.

[51] Int. Cl.$^4$ .............................................. A61K 31/74
[52] U.S. Cl. ...................................... 424/79; 514/653; 514/781; 514/964
[58] Field of Search ........................... 424/79; 514/653

[56] References Cited

U.S. PATENT DOCUMENTS 2,990,332  6/1961  Keating .................................. 424/79
4,221,778  9/1980  Raghunathan ......................... 424/31

FOREIGN PATENT DOCUMENTS 2246037  4/1974  Fed. Rep. of Germany .

OTHER PUBLICATIONS

Lachman et al., "The Theory & Practice of Industrial Pharmacy", 2nd ed, 1976, pp. 374–5.

Primary Examiner—Leonard Schenkman
Attorney, Agent, or Firm—Seidel, Gonda, Lavorgna & Monaco

[57] ABSTRACT

Controlled release pharmaceutical preparations containing coated sulfonic acid cationic exchange resin drug complex particles, the resin particles having been treated, prior to coating, with about 15 to 25% by weight of glycerin, based on the combined weight of the glycerin and the drug resin complex particles.

8 Claims, No Drawings

CONTROLLED RELEASE PHARMACEUTICAL PREPARATIONS

This application is a continuation of application Ser. No. 631,979, filed July 18, 1984.

The present invention relates to sulfonic and cationic exchange resins which have been treated with a critical amount of glycerin to enhance their coatability, to methods for treating the resins with the glycerin, and to selective, prolonged continuous release pharmaceutical preparations containing a sulfonic acid cationic exchange resin having a pharmacologically active monobasic drug absorbed thereon to provide a drug resin complex, wherein at least a portion of the resin is treated with a critical amount of glycerin and provided with a different barrier coating.

BACKGROUND

U.S. Pat. No. 4,221,778 discloses that controlled (i.e., selective, prolonged) continuous release of pharmacologically active drugs, under conditions such as those encountered in the gastrointestinal tract, can be achieved by the application of diffusion barrier coatings to ion exchange resin drug complex particles which have been treated, prior to coating, with an impregnating agent selected from polyethylene glycol, propylene glycol, mannitol, lactose, and methylcellulose.

BRIEF SUMMARY OF THE INVENTION

The present invention is concerned with pharmaceutical preparations comprised of sulfonic acid cationic exchange resin particles having a pharmacologically active monobasic drug adsorbed thereon to form drug-resin complex particles, the resin particles having been treated with from about 15 to about 25 percent by weight of glycerin, based on the combined weight of the glycerin and the complex particles, and thereafter coated with a water-permeable diffusion barrier coating, whereby a selective, prolonged continuous release of the drug is obtainable under conditions encountered in the gastrointestinal tract. The coatability of the particles is enhanced by contacting the particles with, e.g., an aqueous solution of the glycerin from about 20 to about 30 percent by weight of glycerin, based on the combined weight of the glycerin and the particles.

By varying the amount of coating, and/or by blending coated drug-resin complex with uncoated drug-resin complex, it is possible to selectively modify the preparation's drug dissolution profile as desired.

Ion exchange resins, drugs, and coatings, and methods for preparing drug-resin complexes, for coating of the complexes, and for selectively modifying the preparation's dissolution profile through blending and/or degree of coating, are disclosed and exemplified in U. S. Pat. No. 4,221,778, said disclosures and examples being herein incorporated by reference.

DETAILED DESCRIPTION

It has been found that a selective, prolonged continuous release of pharmacologically active monobasic drugs, under conditions such as those encountered in the gastrointestinal tract, can be achieved by the application of diffusion barrier coatings to sulfonic acid cationic exchange resin drug complex particles, the resin particles having been treated, prior to coating, with a critical amount of glycerin, i.e., with from about 15 to about 25 percent by weight of glycerin, based on the combined weight of the glycerin and the complex (or about 20 to 30 percent by weight based on the combined weight of the glycerin and the resin), referably from about 17.5 to 25 percent. The resin particles are preferably treated by contacting them with an aqueous solution of the glycerin. As shown in Tables I and II hereinafter, treatment of the complex with 5, 10 or 30 percent glycerin, in comparison to a control using no glycerin, failed to significantly retard the dissolution rate (and in some cases even enhanced the rate), while the use of 20 percent glycerin has been found to result in substantial retardation of the dissolution profile. Similarly, Table III shows that treatment with from 15 to 25 percent glyceroin has been effective, with the most retardation occurring with the use of from 17.5 to 25 percent.

In general, all monobasic drugs, especially those having short biological half-lives in the order of up to about eight hours, are potential candidates for inclusion in the subject preparations. Examples are phenylpropanolamine (PPA), dextromethorphan, codeine, hydrocodone, ephedrine, pseudoephedrine and verapamil. PPA, a sympathomimetic amine drug with a biological half life of 3.9 hours in man and a pKa of 9.4 was chosen as a model drug for use in these illustrative examples. The loading of the drug on the resin particles can be from about 1 to about 90 percent by weight, although 15 to 50 percent is the normal practical range.

The cationic resin is normally used in particle sizes ranging from about 75 to 1000 $\mu$m. The illusrtative examples employ Amberlite IRP-69 resin, a cationic exchange resin consisting of 100-200 mesh (75-150 $\mu$m) fractured resin particles of Amberlite IR-120. The aprent resin of Amberlite IR-120 and Amberlite IRP-69 is described by the manufacturer as gel-type divinylbenzene sulfonic acid cation exchange resin which swells in water with a pH range of 0–14. The resins should not have inherent pharmacological or toxic properties.

Adsorption of the drug onto the ion exchange resin particles to form the drug resin complex is a well known technique as shown in U.S. Pat. Nos. 2,990,332 and 4,221,778. In general the drug is mixed with an aqueous suspension of the resin and the complex is then washed and dried. Adsorption of drug onto the resin may be detected by a change in the pH of the reaction medium.

As shown by the illustrative examples below, such resin drug complexes rapidly release the drug in 0.1 normal hydrochloric acid (0.1N HCl) dissolution medium (which simulates the fluids of the gastrointestinal tract), e.g., an uncoated and untreated Amberlite IRP-69 phenylpropanolamine complex with a 22.5% drug loading released 86.3% of the drug in 1 hour (Control A). Some retardation of this rapid release can be obtained by attempting to coat the complex particles, without glycerin pretreatment, with a diffusion barrier coating, e.g., Control B shows that an 11.1% (applied) coating level 62.8% of the drug was released in 1 hour. It has now been discovered that the efficiency of the coating on the complex particles can be improved and the release of the drug further slowed by treating the resin particles prior to coating with about 15–25% glycerin, resulting in the ability to selectively prolong the release of drugs from drug-resin complexes. For example, as shown in Example 1 (Table I), pretreatment of the complex particles with 20% glycerin and use of an 11.1% coating level resulted in only 49.1% of the drug being released in 1 hour. While the glycerin is normally applied to the drug-resin complex, it may be applied to the resin prior to complexing, as in the case where the resin particles are coated prior to complexing with the drug.

The water-permeable, diffusion barrier coating material can in general be any of the conventional synthetic or natural film-forming materials with diffusion barrier properties and with no inherent pharmacological or toxic properties. Ethylcellulose (U.S.P. grade), a water insoluble film-forming agent was used as the model diffusion barrier membrane material in the illustrative examples. A plasticizer, Durkex 500 vegetable oil, was used to improve the film-forming charateristics of ethylcellulose. The amount of ethylcellulose film coating used depends on the degree of drug release prolongation desired.

Conventional coating solvents (such as ethanol, or a methylene chloride/acetone mixture, or coating emulsions) and coating procedures can be employed to coat the particles. In the illustrative examples, coatings were carried out by using a Wurster coating apparatus. Techniques of fluid bed spray coating are taught, for example, in U.S. Pat. Nos. 3,089,824; 3,117,027; and 3,253,944. The coating is normally applied to the drug resin complex, but alternatively can be applied to the resin before complexing with the drug.

Dissolution data in the following examples demonstrate the the controlled, continuous release of drugs from drug resin complex particles is now obtainable by use of critical amounts of glycerin and of diffusion barrier coatings, and that the dissolution profiles of such complexes are relatively unaffected by conditions encountered in the gastrointestinal tract.

Variation in the amount of coating and/or the use of coated/uncoated complex mixtures can be employed to selectively modify the dissolution profile as desired. In addition to oral administration, the preparations of the subject invention are also suitable for topical, or rectal or vaginal administration in dosages varying over a wide range, for axample, from about 0.1 to about 1000 mg. depending on the nature of the drug and its intended usage. The compositions can take the form of tablets, powders, capsules, liquid suspensions or other conventional dosage forms.

ILLUSTRATIVE EXAMPLES

The following dissolution test apparatus and procedures were used in the examples to simulate conditions encountered in the gastrointestinal tract: Five hundred ml of the dissolution medium (0.1N HCl) was placed in a round bottom flask immersed in a suitable water bath and the temperature allowed to rise to 37°±0.5° C. The flask was equipped with a paddle which was agitated at 100 rpm. The dissolution medium was pumped from the vessel through a cotton filter. Polyethylene tubing carried the filtered media via a peristaltic pump through a 1 cm flow cell of a Beckman model 35 recording spectrophotometer (equipped with a cell changer) and returned it to the vessel. The flow rate was adjusted to 16 ml/minute. In this way, each of the six vessels and a standard could be monitored at 15 minutes or other suitable intervals. The spectrophotometer was operated at 257 nm in a single beam mode to monitor six resin complex samples and one PPA hydrochloride standard. Each dissolution vessel contained resin complex sample equivalent to 90.6 mg of PPA base. The standard PPA solution contained 90.6 mg of PPA base in 500 ml of 0.1 N HCl. Microscopic examinations of particles of resin were carried iut using a Bausch and Lomb low power binocular microscope (objective X3 and eyepiece X10).

Diffusion barrier coatings were carried out using an air suspension coating technique employing a Wurster coating apparatus (such as made by Aeromatic U.S. Inc., Glatt Air Techniques, Inc., and Dairy Equipmwnt Corp. ).

TEST SERIES I

Control A below illustrates the effect of omitting both the glycerin treatment and the diffusion barrier coating, while Control B illustrates the effect of omitting pretreatment of the drug resin complex prior to coating. Comparative Examples 1A, 1B, and 1C illustrate the use of levels of glycerin outside of the critical range disclosed herein.

CONTROL A

Preparation of Uncoated PPA Resin Complex (26% theoretical load):
PPA Hydrochlorode, 32.28 kg
Amberlite IRP-69 Resin, 74.88 kg
Purified Water, 324 liters The Amberlite IRP-69 resin was suspended in 324 liters of purified water in a 100 gallon lined kettle provided with a suitable stirrer. The PPA hydrochloride was then added to the stirring resin slurry. The mixing was continued for two hours. The resin slurry was then transferred to a suitable centrifuge and the resin separated from the aqueous medium. The resin core was then washed with purified water till free of chloride ions. The resin core was then fluid-bed dried to an exit air temperature of 45° and to a moisture of 5-10%. The dried resin complex was found to contain 22.54% PPA. The average particle size was 96 $\mu$m.

The dissolution results obtained on this uncoated resin complex are reported in Table 2 and show very rapid drug release.

CONTROL B

Preparation of Coated, Untreated, PPA Resin Complex

The aboave PPA resin complex was coated in two separate runs as follows, without any glycerin pretreatment, at 11.1% coating:

(a) Seven hundred g of PPA resin complex (Control A) was used in the core material. One thousand one hundred and sixty-seven ml of a coating solution of the following composition was quantitatively applied to the particles:
Ethylcellulose (50 cps)(U.S.P. Grade), 62.5 g Durkex 500 refined vegetable oil, 25.0 g
Acetone, 116.7 ml
Methylene chloride qs, 1167.0 ml The coating is expressed as the percent by weight of the non-volatile coating solids applied (ethylcellulose and Durkex 500). based on the total non-volatile solids (coating applied plus complex). The coating of the core particles was carried out in a 6-inch fluid-bed coating apparatus at the rate of 20 mls/minute (total time 58 minutes). The inlet air temperature was about 42° C. The outlet air temperature range was 23°-29° C. The average size of the coated particle was 102 $\mu$m. The coated particles assayed 20.27% for PPA.

(b) Six hundred g of PPA resin complex (control A) was used as the core material. One thousand ml of a coating solution proportioned as in run (a) was quantatively applied to the particles. The coating of the core particles was carried out in a 6-inch fluid-bed coating apparatus at the rate of 7.1 ml/minute (total time 140 minutes). The inlet air temperature was about 42° C. The outlet air temperature was about 23° C. The average size of the coated particle was 97 μm. The coated particles assayed 19.0% for PPA.

The mean value of the dissolution results from runs (a) and (b) are reported in Table I and show some retardation of drug release.

EXAMPLE I

The PPA resin complex of Control A was treated with glycerin at a 20% level as follows:
PPA Resin Complex, 680 g
Glycerin, 170 g
Purified water, 275 ml The PPA resin complex was taken in a suitabale planetary mixer. The glycerin was dissolved in the purified water and added to the resin complex. They were then mixed for 10 minutes and fluid-bed dried to a moisture content of 5%. The dried treated resin complex was screened through 60 mesh stainless steel screen.

Five hundred and fifty g of the resin complex was used as the core material for applying coating at an 11.1% level. Nine hundred and fifteen ml of a coating solution as in control B was quantitatively applied to the particles. The coatings of the particles was carried out in a 6-inch fluid-bed coating apparatus at the rate of 12.4 ml/minute (total time 74 minutes). The inlet air temperature range was 42°-44° C. The outlet temperature was 22°-24° C. The average size of the coated particle was 107 μm. The coated particles assayed 17.06% for PPA.

The dissolution results are reported in Table I and show significant retardation compared to the controls and to the following comparative examples at 5, 10 and 30% glycerin treatment levels.

COMPARATIVE EXAMPLES 1A, 1B, and 1C

In three separate runs (1A, 1B, and 1C) the PPA resin complex of Control A was impregnated with glycerin at levels of 5%, 10% and 30%, respectively, following the procedure of Example 1. Each treated complex was then coated at a level of 11.1% using a coating solution as described in Control B, the coating being carried out on a 6-inch fluid-bed coating apparatus.

The coatings for runs 1A, 1B, and 1C were done at rates of 15.4, 15.9, and 14.5 ml/minute (for total coating times of 65, 63, and 69 minutes, respectively). The air inlet temperature was about 41° C. in each instance. The outlet air temperatures were 24°-27° C., and 28°-29° C., respectively. The average size of the coated particles was 103, 98, and 133 μm. The coated particles assayed for 18.3%, 18.3% and 14.4% PPA.

The dissolution data are reported in Table I and are not significantly different from Control B (no glycerin pretreatment).

TABLE I

| Example | % PPA Released at: | | | | |
|---|---|---|---|---|---|
| | 0.25 hr | 0.5 hr | 1 hr | 2 hr | 3 hr |
| Control A | 86.6 | 86.2 | 86.3 | 87.3 | 88.1 |
| Control B | 47.7 | 56.8 | 66.2 | 72.0 | 75.2 |
| Example 1 | 37.1 | 43.0 | 49.1 | 55.3 | 58.4 |
| Comp. Ex. 1A | 46.8 | 55.1 | 63.1 | 69.6 | 72.7 |
| Comp. Ex. 1B | 48.8 | 57.8 | 63.8 | 69.6 | 71.8 |
| Comp. Ex. 1C | 55.9 | 63.0 | 69.2 | 74.2 | 77.4 |

Uncoated complex particles (as in Control A) and coated complex particles (as in Example 1) can be mixed so as to match a variety of desired dissolution profiles.

TEST SERIES II

The dissolution results of Control A (the uncoated PPA resin complex) are repeated in Table II. The remaining tests substantially correspond to those of Test Series I except that a 16% coating level is used. The percent glycerin used in Control C, Example 2, and Comparative Examples 2A and 2B is 0%, 20%, and 30%, respectively.

CONTROL C

Preparation of Coated, Untreated, PPA Resin Complex

The PPA rsin complex of Control A was coated in two separate runs as follows, without any glycerin pretreatment, at a 16% coating level:

(a) Five hundred and fifty g. of PPA resin complex (Control A) was used as the core material. One thousand four hundred ml of a coating solution of the following composition was quantitatively applied to the particles.
Ethylcellulose (50 cps), 75.0 g
Durkex 500 refined vegetable oil, 30.0 g
Acetone, 140.0 ml
Methylene chloride qs, 1400.0 ml The coating of the particles was carried out in a 6-inch fluid-bed coating apparatus at the rate of 15.7 ml/minute (total coating time 89 minutes). The inlet air temperature range was 41°-42° C. The outlet air temperature range was 24°-26° C. The average size of the coated particle was 103 μm. The coated particles assayed 19.1% for PPA.

(b) Run (a) was repeated except that the coating was carried out at the rate of 13.7 ml/minute (total coating time 102 minutes). The inlet air temperature range was 41°-59° C. The outlet air temperature range was 20-°23° C. The average size of the coated particle was 88 μm. The coated particles assayed 18.6% for PPA.

The mean value of the dissolution results from runs (a) and (b) are reported in Table II.

EXAMPLE 2

The PPA resin complex core of Example 1 (PPA resin complex treated with glycerin at 20% level) was coated in two separate runs at a 16% coating level as follows:

(a) Five hundred and fifty g of the resin complex of Example I was used as the core material. One thousand four hundred ml of a coating of the composition in Control C was quantitatively applied to the particles. The coating of the particles was carried out in a 6-inch fluid-bed coating apparatus at the rate of 15.2 ml/minute (total coating time 92 minutes). The inlet temperature range was 41°-42° C. The outlet temperature range was 21°-22° C. The average size of the coated particle was 127 μm. The coated particles assayed at 16.6% for PPA.

(b) Run (a) was repeated except that the coating was carried out at the rate of 14.6 ml/minute (total coating time 96 minutes). The inlet temperature range was 42°-56° C. The outlet temperature range was 20°-24° C. The average size of the coated particle was 98 μm. The coated particles assayed 15.8% for PPA.

The mean values of the dissolution results from runs (a) and (b) are reported in Table II and show significant retardation compared to Controls A and C and to the following comparative examples at 10 and 30% glycerin treatment levels.

COMPARATIVE EXAMPLE 2A

The PPA resin complex core of Comparative Example 1B (PPA resin complex impregnated with glycerin at 10% level) was coated at a 16% coating level as follows:

Five hundred and fifty g of the resin complex was used as the core material. One thousand four hundred ml of a coating solution of the composition in control C was quantitatively applied to the particles. The coating of the particles was carried out in a 6-inch fluid-bed coating apparatus at the rate of 13.3 ml/minute (total coating time 105 minutes). The inlet air temperature range was 41°–43° C. The outlet air temperature range was 26°–31° C. The average size of the coated particle was 100 μm. The coated particles assayed 18.3% for PPA.

The dissolution data are reported in Table II and are not significantly different from Control C (with no glycerin pretreatment).

COMPARATIVE EXAMPLE 2B

The PPA resin complex core of Comparative Example 1C (PPA resin complex impregnated with glycerin at 30% level) was coated at a 16% coating level as follows:

Five hundred and fifty grams of the resin complex was used as the core material. One thousand four hundred ml of a coating of the composition in Control C was quantitatively applied to the particles. The coating of the particles was carried out in a 6-inch fluid-bed coating apparatus at the rate 10.8 ml/minute (total coating time 130 minutes). The inlet temperature range was 41°–49° C. The outlet temperature range was 24°–29° C. The average particle size of the coated particle was 177 μm. The coated particle assayed 14.1% for PPA.

The dissolution data are reported in Table II. As with Comparative Example 2A, the dissolution rate has actually been enhanced (relative to Control C) rather than achieving the desired retardation.

TABLE II

| Example: | % PPA Released at: | | | | |
|---|---|---|---|---|---|
| | 0.25 hr | 0.5 hr | 1 hr | 2 hr | 3 hr |
| Control A | 86.6 | 86.2 | 86.3 | 87.3 | 88.1 |
| Control C | 35.2 | 43.9 | 52.2 | 59.2 | 62.4 |
| Example 2 | 26.3 | 31.8 | 38.1 | 44.1 | 47.6 |
| Comp. Ex. 2A | 39.3 | 48.5 | 55.6 | 62.8 | 65.6 |
| Comp. Ex. 2B | 52.3 | 59.3 | 64.4 | 70.3 | 73.5 |

TEST SERIES III

The following tests illustrate that glycerin is effective at a 15 to 25% level, particularly at 17.5 to 25%. A 16% coating level is used as in Test Series II. Control D is uncoated and untreated (with glycerin), while Control E is coated but untreated.

CONTROL D

Preparation of Uncoated, Untreated, PPA Resin Complex:
PPA Hydrochloride, 135 kg
Amberlite XE-69, 319.2 kg
Purified Water, 1010 liters A PPA resin complex was prepared according to the general procedure of Control A, except that the complex was dried at 52°–57° C. in a drying oven to a moisture less than 5%. The dried complex was found to contain 26.10% PPA. The average particle size was 78 μm.

The dissolution results are reported in Table III and show very rapid drug release.

CONTROL E

Preparation of Coated, Untreated, PPA Resin Complex

The PPA Resin Complex of Control D was coated in two separate runs as follows, without any glycerin pretreatment, at 16.0% coating:

(a) Five hundred fifty g of PPA resin complex of Control D was used as the core material. One thousand four hundred ml of a coating solution of the composition of Control C was quantitatively applied to the particles. The coating of the core particles was carried out in a 6 inch fluid-bed coating apparatus at the rate of 16.9 mls/minute (total time 83 minutes). The inlet air temperature range was 32°–35° C. The outlet air temperature range was 21°–23° C. The average size of the coated particle was 96 μm. The coated particles assayed 21.44% for PPA.

(b) Five hundred fifty g of PPA resin complex of Control D was used as the core material. One thousand four hundred ml of a coating solution as in run (a) was quantitatively applied to the particles. The coating of the core particles was carried out in a 6 inch fluid-bed coating apparatus at the rate of 17.3 mls/minute (total time 81 minutes). The inlet air temperature range was 32°–36° C. The outlet air temperature range was 22°–24° C. The average size of the coated particle was 105 μm. The coated particles assayed 21.76% for PPA.

The mean value of the dissolution results from runs (a) and (b) are reported in Table III and show some retardation of drug release.

EXAMPLE 3

The PPA resin complex of Control D was treated with glycerin at a 15% level and coated in two separate runs as follows:
PPA resin complex, 1,020.0 g
Glycerin, 180.0 g
Purfied water, 400.0 ml The PPA resin complex was taken in a suitable planetary mixer. The glycerin was dissolved in the purified water and added to the resin complex. This was then mixed for 15 minutes and fluid-bed dried to a moisture content of 5%. The dried treated resin complex was screened through a 60 mesh stainless steel screen.

(a) Five hundred fifty g of the above impregnated resin complex was used as the core material. One thousand four hundred ml of a coating solution of the composition of Control C was quantitatively applied to the particles. The coating of the particles was carried out in a 6 inch fluid-bed coating apparatus at the rate of 16.3 ml/minute (total coating time 86 minutes). The inlet air temperature range was 32°–33° C. The outlet air temperature range was 22°–23° C. The average size of the coated particle was 96 μm. The coated particles assayed 18.90% for PPA.

(b) Five hundred fifty g of the above impregnated resin complex was used as the core material. One thousand four hundred ml of a coating solution of the composition of Control C was quantitatively applied to the particles. The coating of the particles was carried out in a 6 inch fluid-bed coating apparatus at the rate of 16.7 ml/minute (total coating time 84 minutes). The inlet air temperature range was 32°–37° C. The outlet air temperature range was 20°–22° C. The average size of the coating particle was 90 μm. The coated particles assayed 17.98% for PPA.

The mean value of the dissolution results from runs (a) and (b) are reported in Table III and show substantial retardation in dissolution relative to Control E, although not to the same degree as shown in Examples 4–7.

EXAMPLE 4

The PPA resin complex of Control D was treated with glycerin at a 17.5% level and coated in two separate runs as follows:
PPA resin complex, 990.0 g
Glycerin, 210.0 g
Purified water, 400.0 g The PPA resin complex was taken in a suitable planetary mixer. The glycerin was dissolved in the purified water and added to the resin complex. This was then mixed for 15 minutes and fluid-bed dried to a moisture content of 5%. The dried treated resin complex was screened through a 60 mesh stainless steel screen..

(a) Five hundred fifty g of the above impregnated resin complex was used as the core material. One thousand four hundred ml of a coating solution of the composition of Control C was quantitatively applied to the particles. The coating of the particles was carried out in a 6 inch fluidbed coating apparatus at the rate of 16.5 ml/minute (total coating time 85 minutes). The inlet air temperature was 32° C. The outlet air temperature range was 21°–23° C. The average size of the coated particle was 94 μm. The coated particles assayed 17.98% for PPA.

(b) Five hundred fifty g of the above impregnated resin complex was used as the core material. One thousand four hundred ml of a coating solution of the composition of Control C was quantitatively applied to the particles. The coating of the particles was carried out in a 6 inch fluid-bed coating apparatus at the rate of 16.3 ml/minute (total coating time 86 minutes). The inlet air temperature range was 32°–36° C. The outlet air temperature range was 20°–23° C. The average size of the coated particle was 86 μm. The coated particles assayed 18.60% for PPA.

The mean value of the dissolution results from runs (a) and (b) are reported in Table III and show significant retardation in dissolution compared to those of Control E.

EXAMPLE 5

The PPA resin complex of Control D was treated with glycerin at a 20.0% level and coated in two separate runs as follows:
PPA resin complex, 1,040.0 g
Glycerin, 260.0 g
Purified water, 440.0 ml The PPA resin complex was taken in a suitable planetary mixer. The glycerin was dissolved in the purified water and added to the resin complex. This was then mixed for 15 minutes and fluid-bed dried to a moisture content of 5%. The dried treated resin complex was screened through a 60 mesh stainless steel screen.

(a) Five hundred fifty g of the above impregnated resin complex was used as the core material. One thousand four hundred ml of a coating solution of the composition of Control C was quantitatively applied to the particles. The coating of the particles was carried out in a 6 inch fluid-bed coating apparatus at the rate of 17.1 ml/minute (total coating time 82 minutes). The inlet air temperature range was 32°–38° C. The outlet air temperature range was 21°–24° C. The average size of the coated particle was 94 μm. The coated particles assayed 18.64% for PPA.

(b) Five hundred fifty g of the above impregnated resin complex was used as the core material. One thousand four hundred ml of a coating solution of the composition of Control C was quantitatively applied to the particles. The coating of the particles was carried out in a 6 inch fluid-bed coating apparatus at the rate of 17.5 ml/minute (total coating time 80 minutes). The inlet air temperature range was 32°–36° C. The outlet air temperature range was 22°–24° C. The average size of the coated particle was 122 μm. The coated particles assayed 17.56% for PPA.

The mean value of the dissolution results from runs (a) and (b) are reported in Table III and show significant retardation in dissolution compared to those of Control E.

EXAMPLE 6

The PPA resin complex of Control D was treated with glycerin at a 22.5% level and coated in two separate runs as follows:
PPA resin complex, 930.0 g
Glycerin, 270.0 g
Purified water, 400.0 ml The PPA resin complex was taken in a suitable planetary mixer. The glycerin was dissolved in the purified water and added to the resin complex. This was then mixed for 15 minutes and fluid-bed dried to a moisture content of 5%. The dried treated resin complex was screened through a 60 mesh stainless steel screen.

(a) Five hundred fifty g of the above impregnated resin complex was used as the core material. One thousand four hundred ml of a coating solution of the composition of Control C was quantitatively applied to the particles. The coating of the particles was carried out in a 6 inch fluid-bed coating apparatus at the rate of 16.5 ml/minute (total coating time 85 minutes). The inlet air temperature range was 32°–33° C. The outlet air temperature range was 21°–23° C. The average size of the coated particles was 82 μm. The coated particles assayed 16.7% for PPA.

(b) Five hundred fifty g of the above impregnated resin complex was used as the core material. One thousand four hundred ml of a coating solution of the composition of Control C was quantitatively applied to the particles. The coating of the particles was carried out in a 6 inch fluid-bed coating apparatus at the rate of 16.9 ml/minute (total coating time 83 minutes). The inlet air temperature range was 32°–33° C. The outlet air temperature range was 19°–23° C. The average size of the coated particle was 96 μm. The coated particles assayed 16.20% for PPA.

The mean value of the dissolution results from runs (a) and (b) are reported in Table III and show significant retardation in dissolution compared to those of Control E.

EXAMPLE 7

The PPA resin complex of Control D was treated with glycerin at a 25.0% level and coated in two separate runs as follows:
PPA resin complex, 900.0 g
Glycerin, 300.0 g
Purified water, 400.0 ml The PPA resin complex was taken in a suitable planetary mixer. The glycerin was dissolved in the purified water and added to the resin complex. This was then mixed for 15 minutes and fluid-bed dried to a moisture content of 5%. The dried treated resin complex was screened through a 60 mesh stainless steel screen.

(a) Five hundred fifty g of the above impregnated resin complex was used as the core material. One thousand four hundred ml of a coating solution of the composition of Control C was quantitatively applied to the particles. The coating of the particles was carried out in a 6 inch fluid-bed coating apparatus at the rate of 16.9 ml/minute (total coating time 83 minutes). The inlet air temperature range was 32°–37° C. The outlet air temperature range was 20°–23° C. The average size of the coated particle was 108 μm. The coated particles assayed 16.50% for PPA.

(b) Five hundred fifty g of the above impregnated resin complex was used as the core material. One thousand four hundred ml of the coating solution of the composition of Control C was quantitatively applied to the particles. The coating of the particles was carried out in a 6 inch fluid-bed coating apparatus at the rate of 15.7 ml/minute (total coating time 89 minutes). The inlet air temperature range was 32°–37° C. The outlet air temperature range was 21°–23° C. The average size of the coated particle was 100 μm. The coated particles assayed 16.38% for PPA.

The mean value of the dissolution results from runs (a) and (b) are reported in Table III and shows significant retardation in dissolution compared to those on Control E.

TABLE III

| Example | % PPA Released at: | | | | |
|---|---|---|---|---|---|
| | 0.25 hr | 0.5 hr | 1 hr | 2 hr | 3 hr |
| Control D | 81.7 | 81.3 | 81.6 | 82.6 | 82.7 |
| Control E | 40.2 | 53.0 | 64.9 | 75.0 | 81.3 |
| Example 3 | 42.5 | 50.7 | 59.1 | 68.8 | 73.9 |
| Example 4 | 41.4 | 47.6 | 53.7 | 59.5 | 62.8 |
| Example 5 | 36.6 | 44.1 | 51.6 | 59.2 | 63.6 |
| Example 6 | 41.5 | 48.6 | 54.9 | 58.3 | 63.6 |
| Example 7 | 41.6 | 46.7 | 53.3 | 59.4 | 62.7 |

Applying the foregoing discovery, controlled release dosage forms can be formulated for human or veterinary use to contain suitable mixtures of coated and uncoated complex particles such that a desired controlled release profile of the drug is obtained. The dosage forms can be solid (such as powders, capsules and tablets) or liquid (such as a suspension of complex particles in a palatable vehicle).

What is claimed is:

1. Sulfonic acid catonic exchange resin particles having a monobasic drug adsorbed thereon, which resin particles have been treated with from about 15 to about 30 percent by weight of glycerin, based on the combined weight of the glycerin and the drug-resin particles, which particles have been subsequently individually coated with a water-permeable diffusion barrier.

2. Resin particles as in claim 1, which resin particles have been treated with from about 15 to about 25 percent by weight of glycerin, based on the combined weight of the glycerin and the drug-resin particles.

3. Resin particles according to claim 1, wherein the diffusion barrier coating comprises ethylcellulose.

4. A process for enhancing the coatability of sulfonic acid catonic exchange resin particles which comprises contacting said particles with an aqueous solution of glycerin containing from about 20% to about 30% by weight of glycerin, based on the combined weight of the glycerin and the particles, and subsequently individually coating said particles with a water-permeable diffusion barrier.

5. A pharmaceutical preparation comprising sulfonic acid cationic exchange resin particles having a pharmacologically active monobasic drug adsorbed thereon to form drug-resin complex particles, which resin particles have been treated with from about 15 to about 25 percent by weight of glycerin, based on the combined weight of the glycerin and the complex particles, and subsequently individually coated with a water-permeable diffusion barrier comprised of ethylcellulose.

6. A pharmaceutical preparation as in claim 5 wherein the resin particles have been treated with from about 17.5 to about 25 percent by weight of glycerin.

7. A pharmaceutical preparation as in claim 6 wherein the drug is phenylpropanolamine.

8. A pharmaceutical preparation as in claim 6 wherein the resin is gel-type divinylbenzene sulfonic acid cationic exchange resin.

* * * * *